US009045509B2

(12) United States Patent
Dussarrat et al.

(10) Patent No.: US 9,045,509 B2
(45) Date of Patent: Jun. 2, 2015

(54) HAFNIUM- AND ZIRCONIUM-CONTAINING PRECURSORS AND METHODS OF USING THE SAME

(75) Inventors: Christian Dussarrat, Wilmington, DE (US); Vincent M. Omarjee, Grenoble (FR); Venkateswara R. Pallem, Hockessin, DE (US)

(73) Assignee: American Air Liquide, Inc., Houston, TX (US)

( * ) Notice: Subject to any disclaimer, the term of this patent is extended or adjusted under 35 U.S.C. 154(b) by 366 days.

(21) Appl. No.: 13/390,452

(22) PCT Filed: Aug. 13, 2010

(86) PCT No.: PCT/US2010/045506
§ 371 (c)(1),
(2), (4) Date: May 7, 2012

(87) PCT Pub. No.: WO2011/020042
PCT Pub. Date: Feb. 17, 2011

(65) Prior Publication Data
US 2012/0207927 A1    Aug. 16, 2012

Related U.S. Application Data

(60) Provisional application No. 61/233,912, filed on Aug. 14, 2009.

(51) Int. Cl.
*C23C 16/18* (2006.01)
*C07F 17/00* (2006.01)

(52) U.S. Cl.
CPC .............. *C07F 17/00* (2013.01); *C23C 16/18* (2013.01)

(58) Field of Classification Search
None
See application file for complete search history.

(56) References Cited

U.S. PATENT DOCUMENTS

| | | | | |
|---|---|---|---|---|
| 5,130,172 | A * | 7/1992 | Hicks et al. | 427/584 |
| 8,399,056 | B2 * | 3/2013 | Blasco et al. | 427/255.31 |
| 8,470,402 | B2 * | 6/2013 | Dussarrat et al. | 427/255.31 |
| 8,546,276 | B2 * | 10/2013 | Gatineau et al. | 438/785 |
| 8,636,845 | B2 * | 1/2014 | Gatineau et al. | 117/104 |
| 2008/0102205 | A1 | 5/2008 | Barry et al. | |
| 2008/0119098 | A1 | 5/2008 | Palley et al. | |
| 2008/0176375 | A1 | 7/2008 | Erben et al. | |
| 2009/0233439 | A1 | 9/2009 | Park et al. | |

FOREIGN PATENT DOCUMENTS

| | | |
|---|---|---|
| JP | 2005 171291 | 6/2005 |
| KR | 2007 0121281 | 12/2007 |
| KR | 2008 0101040 | 11/2008 |
| WO | WO 96 27032 | 9/1996 |
| WO | WO 2006 036045 | 4/2006 |
| WO | WO 2007 066546 | 6/2007 |
| WO | WO 2007 140813 | 12/2007 |
| WO | WO 2007 141059 | 12/2007 |
| WO | WO2007140813 | * 12/2007 .............. C23C 16/18 |
| WO | WO 2008 137239 | 11/2008 |
| WO | WO 2009 036046 | 3/2009 |
| WO | WO 2009 094262 | 7/2009 |
| WO | WO 2009 106433 | 9/2009 |

OTHER PUBLICATIONS

Gott, A. et al., "Chiral alkoxide functionalized guanidinates from ring-opening rearrangement of aminooxazolinate complexes," Organometallics 2007, 26, pp. 136-142.
Irigoyen, A.M. et al., "Synthesis and characterization of chlorobis(dialkylamido) and alkylbis(dialkylamido) derivatives of [($\eta^5$-$C_5Me_5$)$MCl_3$](M = Ti,Zr)," Journal of Organometallic Chemstiry 1995, 494, pp. 255-259.
Besancon, B. et al., "Comparison of $HfSiO_2$ thin film deposited by ALD with moisture using different silicon sources," Abstract #1546, $218^{th}$ ECS Meeting, The Electrochemical Society 2010, 1 pg.
Hermann, W. et al., "Unsymmetrical *ansa*-metallocenes of zirconium and hafnium," Journal of Organometallic Chemistry 1996, vol. 506, pp. 351-355.
Niinisto, J. et al., "Novel mixed alkylamido-cyclopentadienyl precursors for ALD of $ZrO_2$ thin films," Journal of Materials Chemistry 2008, 18, pp. 5243-5247.
Rushworth, S. et al., "Thermal stability studies for advanced hafnium and zirconium ALD precursors," Surface & Coatings Technology 201 (2007), pp. 9060-9065.
Sengupta, S. et al., "Synthesis, physic-chemical and antimicrobial studies on acetylferrocenyl hydrazone derivatives of dichlorobis(cyclopentadienyl) hafnium(IV)," Transition Metal Chemistry 1999, pp. 703-707.
International Search Report and Written Opinion for corresponding PCT/US2010/045506, Apr. 20, 2011.
Bai, Y. et al., "Synthesis and structures of (monoorganyl)amides and —imides of zirconium and hafnium," Chem. Ber. 1992, 125, 825-831.
Driess, M. et al., "P—H activation by zirconium amido complexes: from new phosphanidozirconium complexes to the first $Zr_2P_6$ cluster with the [RP—P—PR]$^3$ ligand [R = $Me^2$($i$P$rMe_2$C)Si]," Eur. J. Inorg. Chem. 2002, 2961-2964.
Galakhov, M. et al., "Carbonyl insertions into metal-nitrogen bonds of Group 4 dialkylamido complexes. X-ray structure of $Cp*(Me_2N)_2Ti[O(Me_2N)C]W(CO)_6$," Organometallics 1995, 14, 131-136.

(Continued)

*Primary Examiner* — Mandy Louie
(74) *Attorney, Agent, or Firm* — Patricia E. McQueeney

(57) ABSTRACT

Disclosed are hafnium- and zirconium-containing precursors and methods of providing the same. The disclosed precursors include a ligand and at least one aliphatic group as substituent selected to have greater degrees of freedom than the usual substituents. The disclosed precursors may be used to deposit hafnium- or zirconium-containing layers using vapor deposition methods such as chemical vapor deposition or atomic layer deposition.

13 Claims, 1 Drawing Sheet

(56) References Cited

OTHER PUBLICATIONS

Gott, A.L. et al., "Catalytic alkene cyclohydroamination via an imido mechanism," Chem. Commun. 2008, 1422-1424.

Haaland, A. et al., "Molecular structures of tris(dimethylamido)-pentamethy-1-cyclopentadienyl-titanium and —zirconium, $(\eta\text{-}C_5Mr_5)M(NMe_2)_3$, M = Ti or Zr, by gas electron diffraction; DFT calculations on the model compound $(\eta\text{-}C_5H_5)Ti(NMe_2)_3$," Journal of Molecular Structure 567-568 (2001) 296-301.

Vollmerhaus, R. et al., "Synthesis and structure of Group 4 iminophosphonamide complexes," Organometallics 2005, 24, 494-507.

* cited by examiner

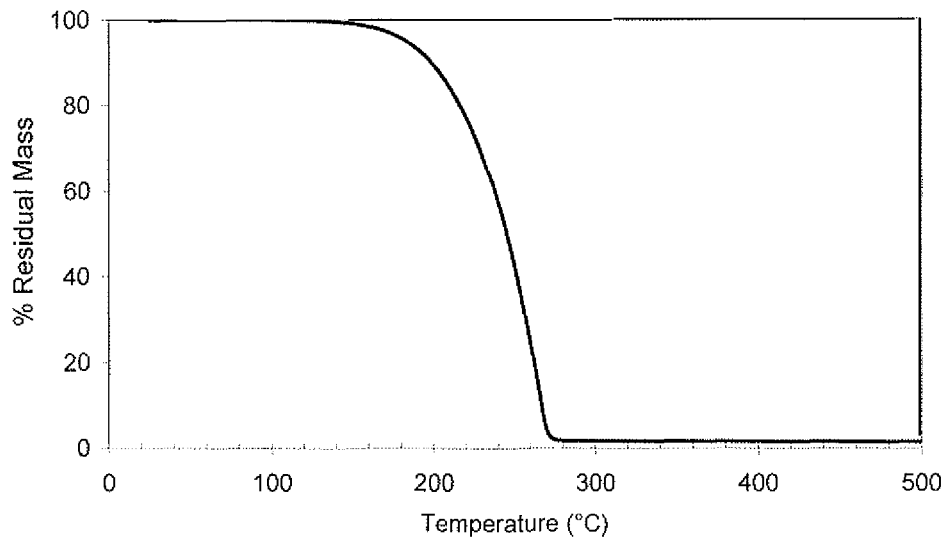
Figure 1. TGA spectra of Me$_5$CpZr(NMe$_2$)$_3$
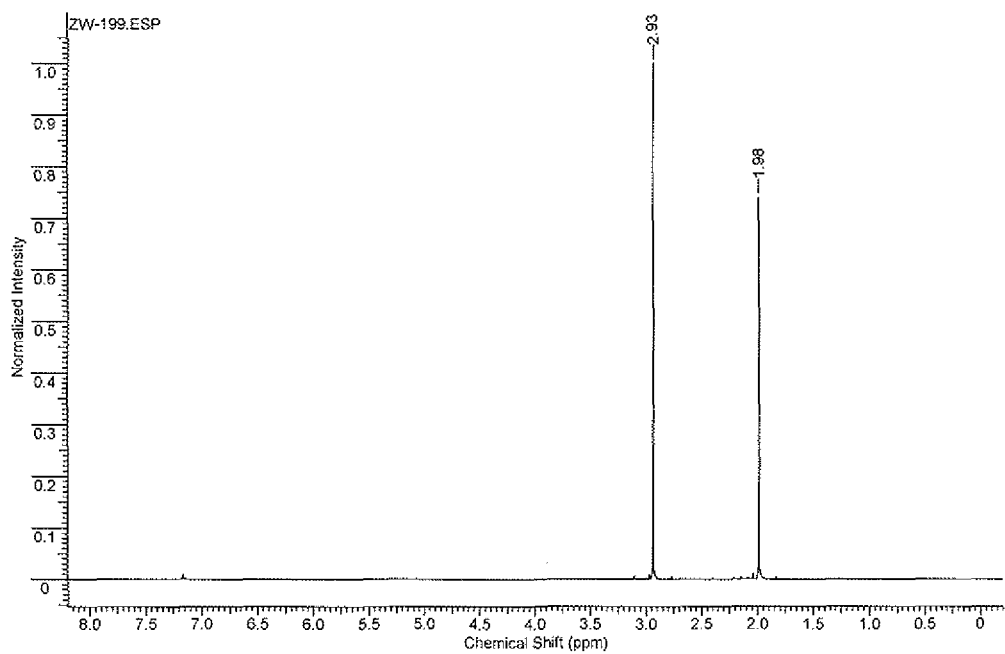
Figure 2: Proton NMR spectra of Me$_5$CpZr(NMe$_2$)$_3$ in C$_6$D$_6$

HAFNIUM- AND ZIRCONIUM-CONTAINING PRECURSORS AND METHODS OF USING THE SAME

CROSS REFERENCE TO RELATED APPLICATIONS

This application is a 371 of International PCT Application PCT/US2010/045506, filed Aug. 13, 2010, which claims priority to U.S. provisional application No. 61/233,912, filed Aug. 14, 2009, the entire contents of each being incorporated herein by reference.

TECHNICAL FIELD

The disclosed hafnium- and zirconium-containing precursors may be used in vapor deposition methods, preferably ALD or PEALD, of manufacturing of semiconductor, photovoltaic, LCD-TFT, or flat panel type devices.

BACKGROUND

One of the serious challenges the industry faces is developing new gate dielectric materials for DRAM and capacitors. For decades, silicon dioxide ($SiO_2$) was a reliable dielectric. However, as transistors have continued to shrink and the technology has moved from "Full Si" transistor to "Metal Gate/High-k" transistors, the reliability of the $SiO_2$-based gate dielectric is reaching its physical limits. One solution is to use other materials for gate dielectrics, such as hafnium-based or zirconium-based metal oxides. These high-k materials (so-called because of their high dielectric constant) can be made much thicker than $SiO_2$ while achieving the same gate capacitance.

Amino hafnium- and zirconium-containing compounds with substituted cyclopentadienyl ligands have been described. See, e.g. Niinisto et al., Journal of Materials Chemistry (2008), 18(43), 5243-5247; WO2007/066546 to Tri Chemical Laboratories, Inc.; WO2007/140813 to L'Air Liquide Societe Anonyme Pour L'etude et L'exploitation Des Procedes Georges Claude; KR2007-0121281 to DNF Co Ltd; US2008/0102205 to Barry et al.; KR10-2008-0101040 to UP Chemical Co Ltd; and WO2009/036046 to Sigma-Aldrich Co.

The stability of these molecules may result in narrower deposition process windows. Therefore a need remains for novel hafnium- and zirconium-containing precursors.

Notation and Nomenclature

Certain terms are used throughout the following description and claims to refer to various components and constituents.

The standard abbreviations of the elements from the periodic table of elements are used herein. It should be understood that elements may be referred to by these abbreviations (e.g., Hf refers to hafnium, Zr refers to zirconium, Pd refers to palladium, Co refers to cobalt, etc).

As used herein, the term "aliphatic group" refers to a group of organic compounds which are carbon atoms are linked in open chains, such as alkanes, alkenes and alkynes; the term "alkyl group" refers to saturated functional groups containing exclusively carbon and hydrogen atoms. Further, the term "alkyl group" may refer to linear, branched, or cyclic alkyl groups. Examples of linear alkyl groups include without limitation, methyl groups, ethyl groups, propyl groups, butyl groups, etc. Examples of branched alkyls groups include without limitation, isopropyl groups, t-butyl groups, etc. Examples of cyclic alkyl groups include without limitation, cyclopropyl groups, cyclopentyl groups, cyclohexyl groups, etc.

As used herein, the abbreviation "CHD" refers to a cyclohexadienyl group; the abbreviation "Cp" refers to a cyclopentadienyl group; the abbreviation "Me" refers to a methyl group; the abbreviation "Et" refers to an ethyl group; the abbreviation "iPr" refers to an isopropyl group; and the abbreviation "t-Bu" refers to a tertiary butyl group.

As used herein, the term "independently" when used in the context of describing R groups should be understood to denote that the subject R group is not only independently selected relative to other R groups bearing the same or different subscripts or superscripts, but is also independently selected relative to any additional species of that same R group. For example in the formula $MR^1_x(NR^2R^3)_{(4-x)}$, where x is 2 or 3, the two or three $R^1$ groups may, but need not be identical to each other or to $R^2$ or to $R^3$. Further, it should be understood that unless specifically stated otherwise, values of R groups are independent of each other when used in different formulas.

SUMMARY

Disclosed are compounds having the formula $ML(NR_7R_8)_3$, wherein M is Hf or Zr, L is a cyclohexadienyl ligand or a pentamethylcyclopenta-dienyl ligand, and $R_7$ and $R_8$ are independently selected from H or an aliphatic group (preferably an aliphatic moiety) having 1 to 6 carbon atoms. The disclosed compounds may include one or more of the following aspects:

the compound being selected from (pentamethylcyclopentadienyl) tris(dimethylamido)hafnium or (pentamethylcyclopentadienyl)tris (dimethylamido)zirconium;

L being the cyclohexadienyl ligand and the compound having the formula:

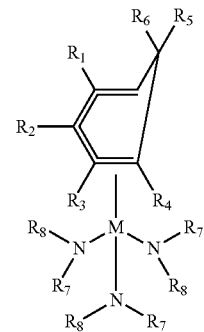

with $R_1$, $R_2$, $R_3$, $R_4$, $R_5$, and $R_6$ being independently selected from H or an aliphatic group (preferably an aliphatic moiety) having 1 to 6 carbon atoms;

at least 3 of $R_1$, $R_2$, $R_3$, $R_4$, $R_5$, and $R_6$ are not H; and the compound being (trimethylcyclohexadienyl)tris(dimethylamido) hafnium or (trimethylcyclohexadienyl)tris (dimethylamido)zirconium.

Also disclosed are methods of forming a hafnium- or zirconium-containing layer on a substrate disposed in a reactor. A vapor comprising at least one compound of any one of the disclosed compounds is introduced into the reactor. The hafnium- or zirconium-containing layer is formed on the substrate using a vapor deposition process. The disclosed method may include one or more of the following aspects:

introducing into the reactor a vapor comprising at least one second precursor;

a metal of the at least one second precursor being selected from the group consisting of Ti, Ta, Bi, Hf, Zr, Pb, Nb, Mg, Al, Sr, Y, Ba, Ca, lanthanides, and combinations thereof;

the hafnium- or zirconium-containing layer being a hafnium oxide layer or a zirconium oxide layer;

the hafnium- or zirconium-containing layer being a hafnium silicate layer or a zirconium silicate layer;

introducing at least one co-reactant into the reactor;

the co-reactant being selected from the group consisting of $O_2$, $O_3$, $H_2O$, $H_2O_2$, NO, $NO_2$, a carboxylic acid, and combinations thereof;

the vapor deposition process being a chemical vapor deposition process; and the vapor deposition process being an atomic layer deposition process.

BRIEF DESCRIPTION OF THE FIGURES

For a further understanding of the nature and objects of the present invention, reference should be made to the following detailed description, taken in conjunction with the accompanying drawings, wherein:

FIG. 1 a graph of thermogravimetric analysis (TGA) data demonstrating percent of weight loss vs. temperature of $(Me_5Cp)Zr(NMe_2)_3$; and FIG. 2 is proton NMR spectra of $(Me_5Cp)Zr(NMe_2)_3$ in $C_6D_6$.

DETAILED DESCRIPTION OF PREFERRED EMBODIMENTS

Disclosed herein are non-limiting embodiments of methods and compounds which may be used in the manufacture of semiconductor, photovoltaic, LCD-TFT, or flat panel type devices.

Disclosed are hafnium- and zirconium-containing precursors. Also disclosed are methods of using the disclosed hafnium- and zirconium-containing precursors to deposit hafnium- and zirconium-containing layers on a substrate.

The disclosed hafnium- and zirconium-containing precursors have the formula $ML(NR_7R_8)_3$, wherein M is Hf or Zr, L is a cyclohexadienyl ("CHD") ligand or a pentamethylcyclopentadienyl ($Me_5Cp$) ligand, and $R_7$ and $R_8$ are independently selected from H or an aliphatic group (preferably an aliphatic moiety) having 1 to 6 carbon atoms.

Preferably, the disclosed hafnium- and zirconium-containing compounds have suitable properties for vapor depositions methods, such as high vapor pressure, low melting point (preferably being in liquid form at room temperature), low sublimation point, and high thermal stability.

Applicants have found that using cyclohexadienyl groups or pentamethylcyclopentadienyl groups may lead to compounds having higher thermal stability which may provide a wide process window while achieving high growth-rate. Without being limited by theory, Applicants believe that a pentamethylcyclopentadienyl group or a cyclohexadienyl group may stabilize the Hf—N or Zr—N bond therefore improving the thermal stability of the molecule while not degrading the overall reactivity of the compound.

Exemplary hafnium or zirconium pentamethylcyclopentadienyl compounds may be selected from $M(Me_5Cp)(NMe_2)_3$, $M(Me_5Cp)(NEt_2)_3$, $M(Me_5Cp)(NMeEt)_3$, $M(Me_5Cp)(NMeiPr)_3$, $M(Me_5Cp)(NMetBu)_3$, $M(Me_5Cp)(NMe_2)_x(NMeEt)_y$, $M(Me_5Cp)(NEt_2)_x(NMeEt)_y$, $M(Me_5Cp)(NMeiPr)_x(NMe_2)_y$, and combinations thereof, with x=1 when y=2 and x=2 when y=1.

The disclosed hafnium- or zirconium-containing compounds may include (pentamethylcyclopentadienyl)tris(dimethylamido)hafnium, $(Me_5Cp)Hf(NMe_2)_3$, or (pentamethylcyclopentadienyl)tris (dimethylamido)zirconium, $(Me_5Cp)Zr(NMe_2)_3$.

The disclosed pentamethylcyclopentadienyl hafnium- or zirconium-containing compounds may be prepared by addition of $HNR_7R_8$ to a cold BuLi/hexane solution. The mixture may be stirred for approximately one hour followed by cooling to approximately 0° C. $Me_5CpMCl_3$ may be added to the cooled mixture. The resulting mixture is then stirred at room temperature overnight. The mixture is filtered and solvent evaporated under vacuum to produce the crude $M(Me_5Cp)(NR_7R_8)_3$ product, which may be purified by known methods. All of the starting materials are commercially available.

To produce the disclosed pentamethylcyclopentadienyl hafnium- or zirconium-containing compounds having different amido ligands (i.e. $M(Me_5Cp)(NR_7R_8)_2(NR_7R_3)$), two different pentamethylcyclopentadienyl compounds produced by the method described above and having the desired amido ligand are mixed in hexane overnight, after which the solvent is evaporated. The resulting crude product may be purified by known methods.

In a second embodiment, the disclosed hafnium- or zirconium-containing compounds have a cyclohexadienyl ligand and the following formula:

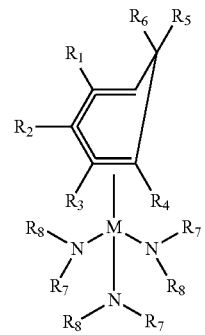

with $R_1$, $R_2$, $R_3$, $R_4$, $R_5$, and $R_6$ being independently selected from H or an aliphatic group (preferably an aliphatic moiety) having 1 to 6 carbon atoms. In this embodiment, Applicants believe that the carbon atom that is out of the plane on the cyclohexadienyl (CHD) ligand may lower the melting point of the resulting compound. Preferably, at least 3 of $R_1$, $R_2$, $R_3$, $R_4$, $R_5$, and $R_6$ are not H.

Exemplary hafnium or zirconium cyclohexadienyl compounds may be selected from $M(R^1-R^6CHD)(NMe_2)_3$, $M(R^1-R^6CHD)(NEt_2)_3$, $M(R^1-R^6CHD)(NMeEt)_3$, $M(R^1-R^6CHD)(NMeiPr)_3$, $M(R^1-R^6CHD)(NMetBu)_3$, $M(R^1-R^6CHD)(NMe_2)_x(NMeEt)_y$, $M(R^1-R^6CHD)(NEt_2)_x(NMeEt)_y$, $M(R^1-R^6CHD)(NMeiPr)_x(NMe_2)_y$, and combinations thereof, with $R^1$-$R^6$ defined above, x=1 when y=2, and x=2 when y=1.

The disclosed hafnium- or zirconium-containing compounds may include (trimethylcyclohexadienyl)tris(dimethylamido)zirconium, $(Me_3CHD)Zr(NMe_2)_3$, and (trimethylcyclohexadienyl)tris(dimethylamido) hafnium, $(Me_3CHD)Hf(NMe_2)_3$.

The disclosed cyclohexadienyl hafnium- or zirconium-containing compounds may be prepared by addition of HNR$_7$R$_8$ to a cold BuLi/hexane solution. The mixture may be stirred for approximately one hour followed by cooling to approximately 0° C. (R$_{1-6}$CHD)MCl$_3$, which may be made by known methods, may be added to the cooled mixture. The resulting mixture is then stirred at room temperature overnight. The mixture is filtered and solvent evaporated under vacuum to produce the crude M(R$^1$-R$^6$CHD)(NR$_7$R$_8$)$_3$ product, which may be purified by known methods. Except for (R$_{1-6}$CHD)MCl$_3$, which may be produced by methods disclosed in the art, all of the starting materials are commercially available.

To produce the disclosed cyclohexadienyl hafnium- or zirconium-containing compounds having different amido ligands (i.e. M(R$_{1-6}$CHD)(NR$_7$R$_8$)$_2$(NR$_7$R$_8$)), two different cyclohexadienyl compounds produced by the method described above and having the desired amido ligand are mixed in hexane overnight, after which the solvent is evaporated. The resulting crude product may be purified by known methods.

The disclosed methods form a hafnium- or zirconium-containing layer on a substrate (e.g., a semiconductor substrate or substrate assembly) using the disclosed precursors in a vapor deposition process. The method may be useful in the manufacture of semiconductor structures. The method includes: providing a reactor and at least one substrate disposed therein; introducing a vapor comprising the disclosed compounds into the reactor; and forming the hafnium- or zirconium-containing layer on the substrate.

The thin film may be deposited from the disclosed precursors using any vapor deposition methods known to those of skill in the art. Examples of suitable deposition methods include without limitation, Chemical Vapor Deposition (CVD), Low Pressure CVD (LPCVD), Plasma Enhanced CVD (PECVD), pulse PECVD, Atomic Layer Deposition (ALD), Plasma Enhanced ALD (PE-ALD), or combinations thereof. Preferably, the deposition process is selected from ALD, PEALD, or combinations thereof. The plasma processes may utilize direct or remote plasma sources.

The disclosed precursor may be supplied either in neat form or in a blend with a suitable solvent, such as ethyl benzene, xylenes, mesitylene, decane, dodecane. The disclosed precursor may be present in varying concentrations in the solvent.

The neat or blended precursor is introduced into a reactor in vapor form. The precursor in vapor form may be produced by vaporizing the neat or blended precursor solution through a conventional vaporization step such as direct vaporization, distillation, or by bubbling. The neat or blended precursor may be fed in liquid state to a vaporizer where it is vaporized before it is introduced into the reactor. Alternatively, the neat or blended precursor may be vaporized by passing a carrier gas into a container containing the disclosed precursor or by bubbling the carrier gas into the disclosed precursor. The carrier gas may include, but is not limited to, Ar, He, N$_2$, and mixtures thereof. Bubbling with a carrier gas may also remove any dissolved oxygen present in the neat or blended precursor solution. The carrier gas and disclosed precursor are then introduced into the reactor as a vapor.

If necessary, the container of disclosed precursor may be heated to a temperature that permits the precursor to be in its liquid phase and to have a sufficient vapor pressure. The container may be maintained at temperatures in the range of, for example, approximately 0° C. to approximately 150° C. Those skilled in the art recognize that the temperature of the container may be adjusted in a known manner to control the amount of precursor vaporized.

The reactor may be any enclosure or chamber within a device in which deposition methods take place such as, and without limitation, a parallel-plate type reactor, a cold-wall type reactor, a hot-wall type reactor, a single-wafer reactor, a multi-wafer reactor, or other types of deposition systems under conditions suitable to cause the precursors to react and form the layers.

The reactor contains one or more substrates onto which the thin films will be deposited. The one or more substrates may be any suitable substrate used in semiconductor, photovoltaic, flat panel or LCD-TFT device manufacturing. Examples of suitable substrates include without limitation silicon substrates, silica substrates, silicon nitride substrates, silicon oxy nitride substrates, tungsten substrates, titanium nitride, tantalum nitride, or combinations thereof. Additionally, substrates comprising tungsten or noble metals (e.g. platinum, palladium, rhodium or gold) may be used. The substrate may also have one or more layers of differing materials already deposited upon it from a previous manufacturing step.

The temperature and the pressure within the reactor are held at conditions suitable for the deposition process. For instance, the pressure in the reactor may be held between about 0.5 mTorr and about 20 Torr, preferably between about 0.2 Torr and 10 Torr, and more preferably between about 1 Torr and 10 Tor, as required per the deposition parameters. Likewise, the temperature in the reactor may be held between about 50° C. and about 600° C., preferably between about 50° C. and about 250° C., and more preferably between about 50° C. and about 100° C.

In addition to the disclosed precursor, a co-reactant may be introduced into the reactor. The co-reactant may be an oxidizing gas, such as oxygen, ozone, water, hydrogen peroxide, nitric oxide, nitrogen dioxide, a carboxylic acid, as well as mixtures of any two or more of these. Alternatively, the co-reactant may be a reducing gas, such as hydrogen, ammonia, a silane (e.g. SiH$_4$, Si$_2$H$_6$, Si$_3$H$_a$), an alkyl silane containing a Si—H bond (e.g. SiH$_2$Me$_2$, SiH$_2$Et$_2$), N(SiH$_3$)$_3$, as well as mixtures of any two or more of these. Preferably the co-reactant is H$_2$ or NH$_3$.

The co-reactant may be treated by a plasma, in order to decompose the co-reactant into its radical form. N$_2$ may also be utilized as a reducing gas when treated with plasma. For instance, the plasma may be generated with a power ranging from about 50 W to about 500 W, preferably from about 100 W to about 200 W. The plasma may be generated or present within the reactor itself. Alternatively, the plasma may generally be at a location removed from the reaction chamber, for instance, in a remotely located plasma system. One of skill in the art will recognize methods and apparatus suitable for such plasma treatment.

The vapor deposition conditions within the chamber allow the disclosed blend and the optional co-reactant to form a hafnium- or zirconium-containing layer on at least one surface of the substrate. In some embodiments, Applicants believe that plasma-treating the optional co-reactant may provide the optional co-reactant with the energy needed to react with the disclosed blend.

Depending on what type of film is desired to be deposited, a second precursor may be introduced into the reactor. The second precursor may be another metal source, such as Ti, Ta, Si, Bi, Hf, Zr, Pb, Nb, Mg, Mn, Ru, Cu, Al, Sr, Y, Ba, Ca, lanthanides, and combinations thereof. Where a second metal-containing precursor is utilized, the resultant film deposited on the substrate may contain at least two different metal types.

The disclosed precursor and any optional co-reactants and precursors may be introduced into the reactor simultaneously (CVD), sequentially (ALD, P-CVD), or in other combinations. The precursors and co-reactants may be mixed together to form a co-reactant/precursor mixture, and then introduced to the reactor in mixture form. Alternatively, the precursors and co-reactants may be sequentially introduced into the reaction chamber and purged with an inert gas between the introduction of the precursors and the introduction of the co-reactants. For example, the disclosed precursor may be introduced in one pulse and two additional metal-containing precursor sources may be introduced together in a separate pulse [modified PE-ALD]. Alternatively, the reactor may already contain the co-reactant species prior to introduction of the disclosed precursor, the introduction of which may optionally be followed by a second introduction of the co-reactant species. In another alternative, the disclosed precursor may be introduced to the reactor continuously while other metal sources are introduced by pulse (pulse PECVD). In each example, a pulse may be followed by a purge or evacuation step to remove excess amounts of the component introduced. In each example, the pulse may last for a time period ranging from about 0.01 seconds to about 30 seconds, alternatively from about 0.3 seconds to about 10 seconds, alternatively from about 0.5 seconds to about 2 seconds.

Depending on the particular process parameters, deposition may take place for a varying length of time. Generally, deposition may be allowed to continue as long as desired or necessary to produce a film with the necessary properties. Typical film thicknesses may vary from several hundred angstroms to several hundreds of microns, depending on the specific deposition process. The deposition process may also be performed as many times as necessary to obtain the desired film.

In one non-limiting exemplary PE-ALD type process, the vapor phase of the disclosed precursor is introduced into the reactor, where it is contacted with a suitable substrate. Excess precursor may then be removed from the reactor by purging and/or evacuating the reactor. A reducing gas (for example, $H_2$) is introduced into the reactor under plasma power where it reacts with the absorbed precursor in a self-limiting manner. Any excess reducing gas is removed from the reactor by purging and/or evacuating the reactor. If the desired film is a hafnium or zirconium film, this two-step process may provide the desired film thickness or may be repeated until a film having the necessary thickness has been obtained.

Alternatively, if the desired film is a bimetal film, the two-step process above may be followed by introduction of the vapor of a metal-containing precursor into the reactor. The metal-containing precursor will be selected based on the nature of the bimetal film being deposited. After introduction into the reactor, the metal-containing precursor is contacted with the substrate. Any excess metal-containing precursor is removed from the reactor by purging and/or evacuating the reactor. Once again, a reducing gas may be introduced into the reactor to react with the metal-containing precursor. Excess reducing gas is removed from the reactor by purging and/or evacuating the reactor. If a desired film thickness has been achieved, the process may be terminated. However, if a thicker film is desired, the entire four-step process may be repeated. By alternating the provision of the disclosed precursor, metal-containing precursor, and co-reactant, a film of desired composition and thickness can be deposited.

The hafnium- or zirconium-containing films or layers resulting from the processes discussed above may include a pure metal (M), a bimetal-containing film ($M_1M_2$) such as a metal silicate ($M_kS_l$) or a metal lanthanide ($M_kLn_l$), metal oxide ($M_nO_m$) or metal oxynitride ($M_xN_yO_z$) film wherein M=Hf or Zr and k, l, m, n, x, y, and z are integers which inclusively range from 1 to 6. Preferably, the metal-containing films are selected from a metal lanthanide, $HfO_2$, or $ZrO_2$. One of ordinary skill in the art will recognize that by judicial selection of the appropriate disclosed precursor, optional metal-containing precursors, and optional co-reactant species, the desired film composition may be obtained.

EXAMPLES

The following non-limiting examples are provided to further illustrate embodiments of the invention. However, the examples are not intended to be all inclusive and are not intended to limit the scope of the inventions described herein.

Example 1

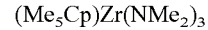
$(Me_5Cp)Zr(NMe_2)_3$

The ligand, $LiNMe_2$, was freshly prepared by addition of $HNMe_2$ (0.186 mol, 8.4 g plus additional 3.6 g was added) into an ice cold bath of BuLi/hexane solution. The resulting mixture was stirred for 1 hour. Again the flask was cooled to 0° C., followed by solid addition of $Me_5CpZrCl_3$ and resulting mixture was stirred at room temperature for overnight. The reaction mixture was filtered, solvent was evaporated from the filtrate under vacuum and a crude yellow solid was obtained. Sublimation of the crude material yielded 18 g (83%) pure product as white solid. FIG. 1 a graph of thermogravimetric analysis (TGA) data demonstrating percent of weight loss vs. temperature of the white solid, $(Me_5Cp)Zr(NMe_2)_3$. FIG. 2 is proton NMR spectra of $(Me_5Cp)Zr(NMe_2)_3$ in $C_6D_6$. $^1H$ NMR ($C_6D_6$, δ): 1.98 (15H, s, $(CH_3)_5C_5$), 2.93 (18H, s, $N(CH_3)_2$).

Prophetic Example 2

$[Me_5Cp]Zr(NMe_2)_2(NMeEt)$

The product of Example 1 may be reacted with $[(CH_3)_5C_5]Zr(NMeEt)_3$, which may be produced by the same method of example 1 using LiNMeEt in place of $LiNMe_2$, in hexane overnight and solvent is evaporated. Crude product may be purified by known methods.

Prophetic Example 3

$[Me_5Cp]Hf(NMe_2)_3$

Is expected to be synthesized by the method developed for the zirconium compound of Example 1, except that instead of $Me_5CpZrCl_3$, $Me_5CpHfCl_3$ will be used in the reaction.

Prophetic Example 4

$(Me_3CHD)Zr(NMe_2)_3$

Is expected to be synthesized by the following procedure. The ligand, $LiNMe_2$, will be freshly prepared by addition of $HNMe_2$ into ice cold bath of BuLi/hexane solution. The resulting mixture will be stirred. Again the flask will be cooled to 0° C., followed by addition of $[(CH_3)_3CHD]ZrCl_3$, which may be made by known methods, and resulting mixture will be stirred at room temperature overnight. The reaction mixture will be filtered; solvent will be evaporated from the filtrate under vacuum, and crude material will be obtained. Purification of crude will result in pure product isolation.

Prophetic Example 5

$(Me_3CHD)Zr(NMe_2)_2(NMeEt)$

The product of Example 4 may be reacted with $[(CH_3)_3CHD]Zr(NMeEt)_3$, which may be produced by the same method of Example 4 using LiNMeEt in place of $LiNMe_2$, in hexane overnight and solvent will be evaporated. Crude product may be purified by known methods.

Prophetic Example 6

$(Me_3CHD)Hf(NMe_2)_3$

Is expected to be synthesized by following procedure. The ligand, $LiNMe_2$, will be freshly prepared by addition of $HNMe_2$ into ice cold bath of BuLi/hexane solution. The resulting mixture will be stirred. Again the flask will be cooled to 0° C., followed by addition of $[(CH_3)_3CHD]HfCl_3$ and stirring the resulting mixture at room temperature for overnight. The reaction mixture will be filtered; solvent will be evaporated from the filtrate under vacuum, and crude material will be obtained. Purification of crude will result in pure product isolation.

It will be understood that many additional changes in the details, materials, steps, and arrangement of parts, which have been herein described and illustrated in order to explain the nature of the invention, may be made by those skilled in the art within the principle and scope of the invention as expressed in the appended claims. Thus, the present invention is not intended to be limited to the specific embodiments in the examples given above and/or the attached drawings.

What is claimed is:

1. A method of forming a hafnium- or zirconium-containing layer on a substrate, the method comprising:
    providing a reactor and at least one substrate disposed therein;
    introducing into the reactor a vapor comprising a compound having the formula

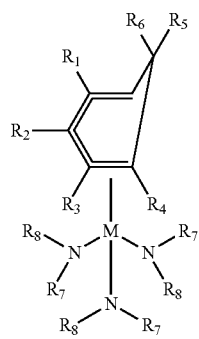

wherein M is Hf or Zr and $R_1$, $R_2$, $R_3$, $R_4$, $R_5$, $R_6$, $R_7$ and $R_8$ are independently selected from H or an aliphatic group having 1 to 6 carbon atoms; and
    forming the hafnium- or zirconium-containing layer on the substrate using a vapor deposition process.

2. The method of claim 1, further comprising introducing into the reactor a vapor comprising at least one second precursor.

3. The method of claim 2, wherein a metal of the at least one second precursor is selected from the group consisting of Ti, Ta, Bi, Hf, Zr, Pb, Nb, Mg, Al, Sr, Y, Ba, Ca, lanthanides, and combinations thereof.

4. The method of claim 1, wherein the hafnium- or zirconium-containing layer is a hafnium oxide layer or a zirconium oxide layer.

5. The method of claim 1, further comprising introducing into the reactor at least one co-reactant.

6. The method of claim 5, wherein the co-reactant is selected from the group consisting of $O_2$, $O_3$, $H_2O$, $H_2O_2$, NO, $NO_2$, a carboxylic acid, and combinations thereof.

7. The method of claim 1, wherein the vapor deposition process is an atomic layer deposition process.

8. The method of claim 1, wherein at least 3 of $R_1$, $R_2$, $R_3$, $R_4$, $R_5$, and $R_6$ are not H.

9. The method of claim 8, wherein the compound is selected from the group consisting of
    (trimethylcyclohexadienyl)tris(dimethylamido)hafnium and
    (trimethylcyclohexadienyl)tris(dimethylamido)zirconium.

10. The method of claim 9, wherein the compound is (trimethylcyclohexadienyl)tris(dimethylamido)hafnium.

11. The method of claim 9, wherein the compound is (trimethylcyclohexadienyl)tris(dimethylamido)zirconium.

12. The method of claim 1, wherein the hafnium- or zirconium-containing layer is a hafnium silicate layer or a zirconium silicate layer.

13. The method of claim 1, wherein the vapor deposition process is a chemical vapor deposition process.

* * * * *